United States Patent [19]

Schroeder

[11] Patent Number: 4,699,137

[45] Date of Patent: Oct. 13, 1987

[54] EXHALATION VALVE

[75] Inventor: Gerhardt P. Schroeder, Madison, Wis.

[73] Assignee: The BOC Group, Montvale, N.J.

[21] Appl. No.: 856,446

[22] Filed: Apr. 23, 1986

Related U.S. Application Data

[63] Continuation of Ser. No. 554,877, Nov. 25, 1983, abandoned.

[51] Int. Cl.⁴ ............................................. A61M 16/00
[52] U.S. Cl. .............................. 128/205.24; 251/61.1; 251/331; 92/99
[58] Field of Search ...................... 128/204.26, 205.24; 251/61.1, 331; 92/7, 99

[56] References Cited

U.S. PATENT DOCUMENTS

| | | | |
|---|---|---|---|
| 2,427,441 | 9/1947 | Butts | 251/61.1 |
| 2,629,375 | 2/1953 | Holmes | 128/205.24 |
| 2,742,785 | 4/1956 | St. Clair | 92/99 |
| 2,847,258 | 8/1958 | Burdick | 251/331 |
| 2,939,676 | 6/1960 | Kilcon | 251/331 |
| 3,078,066 | 2/1963 | Moore | 251/61.1 |
| 3,275,011 | 9/1966 | Berezansky | 251/331 |
| 3,426,999 | 2/1969 | Toinet | 251/331 |
| 3,444,857 | 5/1969 | Godel | 128/205.24 |
| 3,690,344 | 9/1972 | Brumm | 251/61.1 |
| 3,731,594 | 5/1973 | Rannenberg | 92/99 |
| 3,802,462 | 4/1974 | Trosch | 251/61.1 |
| 4,454,893 | 6/1984 | Orchard | 128/205.24 |
| 4,495,854 | 1/1985 | Hibino | 92/99 |

FOREIGN PATENT DOCUMENTS 2450094  5/1975  Fed. Rep. of Germany ..... 251/61.1

Primary Examiner—Henry J. Recla
Attorney, Agent, or Firm—Marshall, O'Toole, Gerstein, Murray & Bicknell

[57] ABSTRACT

An exhalation valve is disclosed having an inlet, an outlet and a diaphragm movable between closed position covering the inlet and an open position away from the inlet. The valve includes a bias means comprising a sealed chamber containing a gas acting upon the diaphragm and urging the diaphragm to its closed position. An opening means in said sealed chamber conducts a control pressure to chamber to create the bias acting against one side of the diaphragm. The diaphragm comprises a flexible peripheral portion and a semi-rigid plunger. The plunger has a projection adapted to move within a confined space to align the diaphragm and provide damping to its movement. The flexible peripheral portion of the diaphragm has a specially shaped cross-section comprising two attached cantilever sections that reduce the effective resistance to motion between open and closed positions. In the preferred embodiment, the plunger is an insert that fits into and is retained by the flexible peripheral portion.

1 Claim, 2 Drawing Figures

EXHALATION VALVE

This application is a continuation of application Ser. No. 554,877, filed Nov. 25, 1983, and now abandoned.

BACKGROUND OF THE INVENTION

The present invention relates to an exhalation valve used in a respiratory breathing circuit and which is utilized to control the exhalation of a patient utilizing that breathing circuit and to control the minimum pressure within that patient circuit.

There are presently various forms of exhalation valves for respiratory breathing circuits. One fairly popular commercial type is the mushroom valve wherein an inflatable bladder is located adjacent an opening through which the patient's exhaled breath passes. By inflating the bladder, that bladder expands to the point where it covers and thus seals the opening and prevents the passage of gas therethrough. One difficulty with such valve is, however, that it may materially deform after prolonged use and fail to provide an adequate seal.

A further type of exhalation valve, as shown in U.S. Pat. No. 4,241,756 includes a flexible diaphragm that covers the opening and a sealed chamber above the diaphragm is selectively pressurized to create a bias urging against the diaphragm to close the same or to retain a bias against that diaphragm urging it toward its closed position.

A difficulty with that flexible diaphragm type of valve is, however, that the flexibility of the diaphragm causes instability thereof, i.e. the diaphragm may not move uniformly from its seat but may flex only in a certain area thereof and thus release pressure in the patient circuit at a level unanticipated by the control pressure in the sealed chamber.

If, on the other hand, the diaphragm is comprised of a rigid material to overcome the flexing problem, the rigid diaphragm does not allow good sealing against the valve opening and leakage is a further difficulty.

SUMMARY OF THE INVENTION

There is here disclosed, an exhalation valve of the diaphragm type and in which an improved diaphragm is utilized having a resilient outer peripheral portion and which surrounds an inner portion or plunger of fairly rigid material and having a damping means to control and stabilize the movement of the diaphragm. As a part of the plunger, a projection extends outwardly therefrom and moves, throughout its stroke, within a suitable shaped cylindrical opening and which serves to align the movement of the diaphragm itself as well as damp its motion.

In the preferred embodiment, the plunger is fitted into the outer peripheral portion for ease in molding and assembly. Thus, the outer peripheral portion of the diaphragm is flexible and thus effects a good seal against the valve opening and yet the rigid plunger provides stability of movement of the overall diaphragm.

The valve itself is relatively simple to manufacture in that the diaphragm is assembled by snapping the plunger into the inner opening of the outer peripheral portion and the diaphragm thus placed over the inlet for gases exhaled from the patient. A cap is snapped over the flexible diaphragm to enclose the same and to form the enclosed chamber which is pressurized to both move the diaphragm to the closed position and to maintain a desired PEEP level of pressure within the patient circuit. The cylindrical opening is formed in the cap and, when the cap is snapped in position, the opening is in alignment with and receives the projection extending from the plunger.

Thus the unique diaphragm having a fairly rigid plunger with a projection extending therefrom and a flexible outer peripheral portion is stabilized in its movement between open and closed positions and yet which provides a good seal about the valve opening.

DESCRIPTION OF PREFERRED EMBODIMENT

Figure 1:
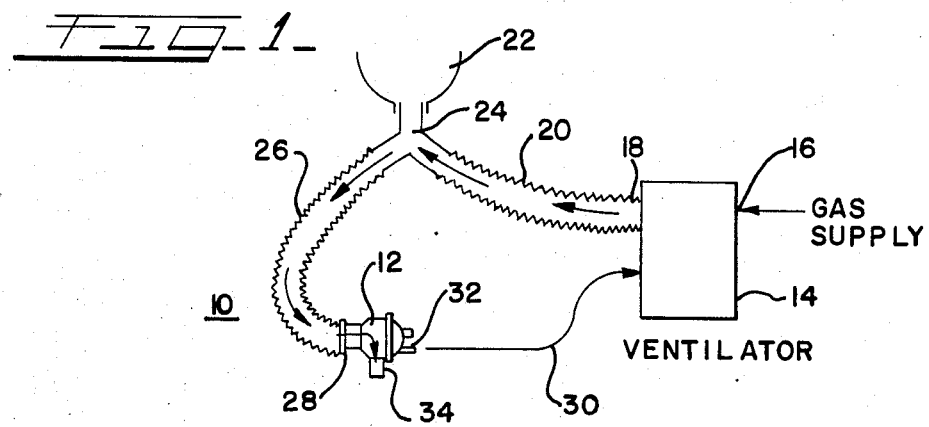
FIG. 1 is a schematic view of a respiratory breathing circuit containing an exhalation valve constructed in accordance with the present invention.

In FIG. 1 there is shown a schematic view of a respiratory breathing circuit 10 in which the exhalation valve 12 of the present invention is utilized. As herein described, exhalation valve 12 will be specifically utilized in an open respiratory breathing circuit, however, the exhalation valve 12 may also be readily used in a closed anesthesia circuit.

In the respiratory breathing circuit 10, as shown, the normal components include a ventilator 14 that supplies the gas to the patients lungs and which also provides a pressure signal for operation of the exhalation valve 12. A supply of gas is made available to the ventilator 14 as is well known in the art via an inlet 16. An outlet 18 from the ventilator 14 is connected to a flexible tubing 20 that carries gas from ventilator 14 to some means of communicating that gas to a patient's lungs. A patient mask 22 is shown which is connectible to flexible tubing 20 by a wye connector 24. A further flexible tubing 26 carries gas from the patient mask 22 and also is connected to wye connector 24.

That flexible tubing 26 carrying exhalation gas from the patient connects to the exhalation valve inlet 28. A small tubing 30 communicates between the ventilator 14 and a port 32 in exhalation valve 12, the purpose of which will be later explained. The small tubing 30 does, however, communicate a pressure signal from ventilator 14 to exhalation valve 12 to control gas passing through exhalation valve 12 between the exhalation valve inlet 28 and exhalation valve outlet 34.

Figure 2:
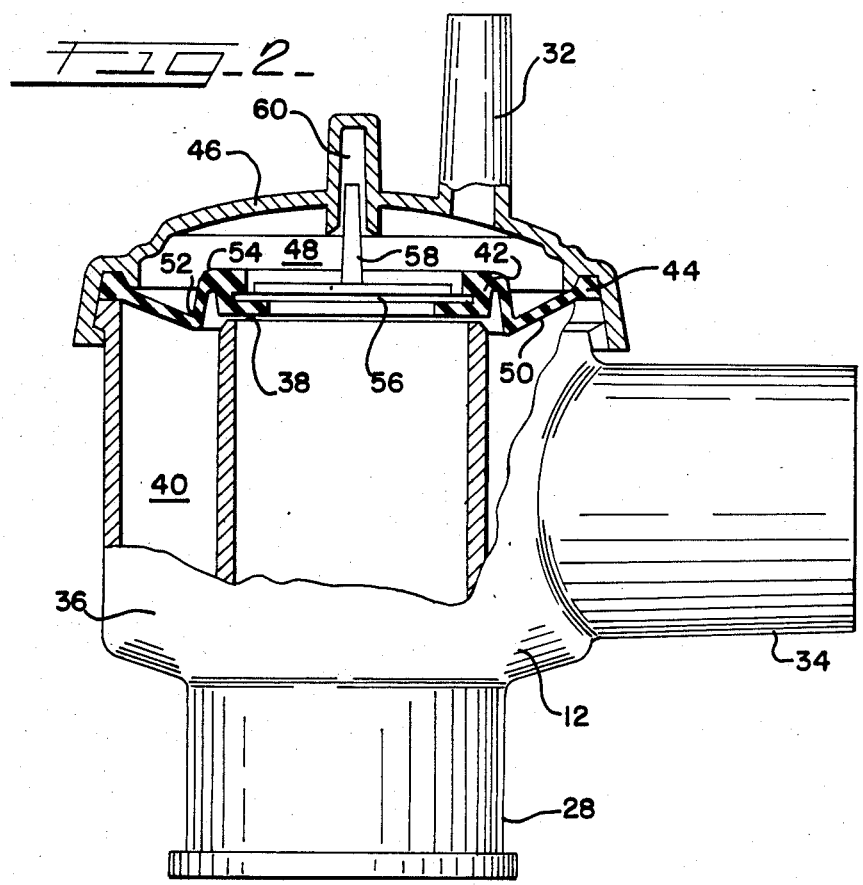
FIG. 2 is a cross-sectional view of the exhalation valve usable with the circuit of FIG. 1.

Turning now to FIG. 2, there is shown a cross-sectional view of the exhalation valve 12 constructed for use in a breathing circuit such as used in FIG. 1, in accordance with this invention. The valve 12 includes a valve housing 36 having inlet 28 and outlet 34.

The inlet 28 is formed within valve housing 36, as shown, as a cylinder which continues upwardly within the housing 36 and forms a valve seat 38 at the top thereof as a round opening.

An annular exhaust chamber 40 surrounds the inlet 28 and communicates directly with the outlet 34.

A flexible diaphragm 42 is positioned atop the valve seat 38 and cooperates therewith to open or close the exhalation valve 12. At the outer peripheral edge of flexible diaphragm 42 there is formed a bead 44 that is sealed between valve housing 36 and a cap 46. The cap 46 is assembled to the valve housing 36 by a snap fit.

A control chamber 48 is thus formed between the cap 46 and the flexible diaphragm 42 and port 32 is formed in cap 46 through which an outside source of pressure can communicate to control the pressure within control chamber 48.

Flexible diaphragm 42 is comprised of a flexible outer peripheral portion 50 having flexible hinges 52 and 54 to enable movement of the flexible diaphragm 42 with minimum resistance. The hinge 52 forms a longer outer cantilever extending inwardly and downwardly from the outer periphery of the diaphragm 42, and the hinge 54 forms a shorter inner cantilever which extends outwardly and downwardly from the center area of the diaphragm. During use of the valve, when the diaphragm moves upwardly from the seat 38, the outer cantilever is forced to bend upwardly and radially inwardly relative to the outer periphery of the diaphragm, and the shorter inner cantilever folds downwardly and toward the valve seat 38. This double bending effect of the cantilever hinges 52 and 54 is advantageous in that it reduces the effective resistant to motion of the center area of the diaphragm and thereby makes the valve faster acting. In the center of flexible diaphragm 42, there is a fairly rigid plunger 56. In the preferred embodiment, the plunger 56 merely snaps into a suitable shaped opening that is molded in the flexible outer peripheral portion 50. The fairly rigid plunger 56 may be constructed of polypropylene while the flexible outer peripheral portion 50 may be of silicone but other flexible materials can be utilized that are preferably sterilizable by autoclave or ethylene oxide. As shown in FIG. 2, the upper and lower sides of the plunger 56 are exposed through the opening of the diaphragm that receives the plunger. Consequently the upper side of the plunger is in direct contact with the gas in the control chamber 48 whereas the lower side of the plunger is in direct contact with the gas in the inlet 28. As a consequence, the plunger 56 senses directly any pressure differences between its upper and lower sides. Since the plunger is relatively rigid, it is not compressed or flexed by a pressure difference and therefore the plunger reacts quickly to pressure differences to open or close the valve. Of course, the flexible part of the diaphragm is engageable with the seat 38 to form a seal. p Extending upwardly from plunger 56 is a projection 58 that rides within cylindrical opening 60 formed in the cap 46.

In the operation of the exhalation valve 12, gases expired from the patient pass into the exhalation valve 12 through the inlet 28. During the time the ventilator is in the inspiration phase, that is, gas is being delivered to the patient by the ventilator, a sufficient control pressure is communicated from ventilator 14 to the control chamber 48 through port 32 to create a force against the flexible diaphragm 42 retaining it in the closed position. In the closed position, not shown, the flexible outer peripheral portion 50 of the flexible diaphragm 42 seals against the valve seat 38 to prevent the passage of gas therethrough, that is, there is no means of communication between the inlet 28 and the outlet 34 of the exhalation valve 12.

As the ventilator ends the inhalation phase and the patient exhales, the pressure communicated through the port 32 by ventilator 14 to control chamber 48 is decreased so that the flexible diaphragm 42 can be raised by the flow of exhalation gas from the patient. Such gas may pass through the exhalation valve 12 from inlet 28 to outlet 34. Opening of the flexible diaphragm 42 is controlled, such as to maintain PEEP, by controlling the pressure, during exhalation, within the control chamber 48 by the ventilator 14.

During opening and closing of exhalation valve 12, the flexible diaphragm 42 is readily moveable by means of flexible hinges 52 and 54 yet retains stability through rigid plunger 56 having its projection 58 retained within cylindrical oPening 60 in cap 46, thus the flexible diaphragm 42 moves up and down in a set path and the movement of flexible diaphragm 42 moves fairly uniformly with respect to valve seat 38 so that opening and closing of exhalation valve 12 is stable, yet good sealing is achieved in the closed position. Since the plunger 56 is directly exposed to the gas pressures on its opposite sides, it reacts quickly to differences in gas pressures, while the flexible part of the diaphragm around the plunger forms a good seal with the valve seat. The flexible hinges 52 and 54 further increase the reaction speed.

While the present invention has been particularly set forth in terms of specific embodiments thereof, it will be understood in view of the instant disclosure, that numerous variations upon the invention are now enabled to those skilled in the art, which variations yet reside within the scope of the instant teaching. Accordingly, the invention is to be broadly construed, and limited only by the scope and spirit of the claims now appended hereto.

I claim:

1. An exhalation valve comprising a valve housing, said valve housing including a main body and a cap fitted thereto, said main body having an inlet and an outlet, a circular valve seat formed in said main body intermediate said inlet and said outlet, an annular flexible diaphragm having first and second faces, a centrally located opening therethrough and an outer periphery, said first face being formed around the periphery of said opening and including a resilient annular portion which is movable against and away from said circular valve seat to, respectively, close and open a flow path from said inlet to said outlet through said circular valve seat, the second face of said diaphragm forming with said cap a closed control chamber, port means in said cap for communicating a control pressure to said closed control chamber for controlling the movement of said flexible diaphragm, a circular rigid plunger including a substantially nonflexing disc, said disc being positioned in said opening and sealingly fixed to said flexible diaphragm, said disc of said plunger overlying said annular portion of said diaphragm, said plunger having a rigid projection extending in said control chamber, a recess formed in said cap and slidingly receiving said projection during movement of said plunger and said flexible diaphragm, said recess snugly receiving said projection to restrain said rigid plunger to movement generally perpendicular to said valve seat, said disc of said plunger being exposed on the opposite sides thereof to gas pressure differences existing between said inlet, said outlet and said control pressure, said diaphragm further including an annular outer periphery retained in position between said main body and said cap, and annular angled hinge means connecting said outer periphery to said resilient annular portion.

* * * * *